United States Patent [19]  
Dadurian et al.

[11] 4,112,522  
[45] Sep. 12, 1978

[54] KNEE-JOINT PROSTHESIS

[76] Inventors: Aram Dadurian, Knochenhauer Strasse 15, D 2800 Bremen; Günther Rehder, Mummelmannstrasse 10, D 2805 Stuhr 3, both of Germany

[21] Appl. No.: 738,978
[22] Filed: Nov. 4, 1976
[30] Foreign Application Priority Data Nov. 4, 1975 [DE] Fed. Rep. of Germany ....... 2549318

[51] Int. Cl.² ................................................ A61F 1/24
[52] U.S. Cl. .......................................... 3/1.91; 3/1.911; 128/92 C
[58] Field of Search ................. 3/1.911, 1.91, 1, 1.912, 3/1.913; 128/92 C, 92 CA

[56] References Cited  
U.S. PATENT DOCUMENTS

| 3,813,700 | 6/1974 | Tavernetti et al. ............... 3/1.911 X |
| 3,909,854 | 10/1975 | Martinez ............................. 3/1.911 |
| 3,934,272 | 1/1976 | Wearne et al. ........................ 3/1.911 |
| 4,001,896 | 1/1977 | Arkangel ............................ 3/1.911 X |

FOREIGN PATENT DOCUMENTS 2,154,338  5/1973  Fed. Rep. of Germany ............ 3/1.911

Primary Examiner—Ronald L. Frinks  
Attorney, Agent, or Firm—Sughrue, Rothwell, Mion, Zinn and Macpeak

[57] ABSTRACT

A knee joint prosthesis has a femur part and a tibia part which are pivotable relative to one another about a joint-flexing axis. One of the parts is rotatable about an axis perpendicular to the flexing axis. An eccentric member, the angular position of which is determined by the degree of joint flex, engages a pair of abutments on the rotatable part so that rotation is only possible when the joint is flexed with the angle of rotation being determined by the size of the gap between the abutments and eccentric member when the joint is in its flexed position.

10 Claims, 4 Drawing Figures

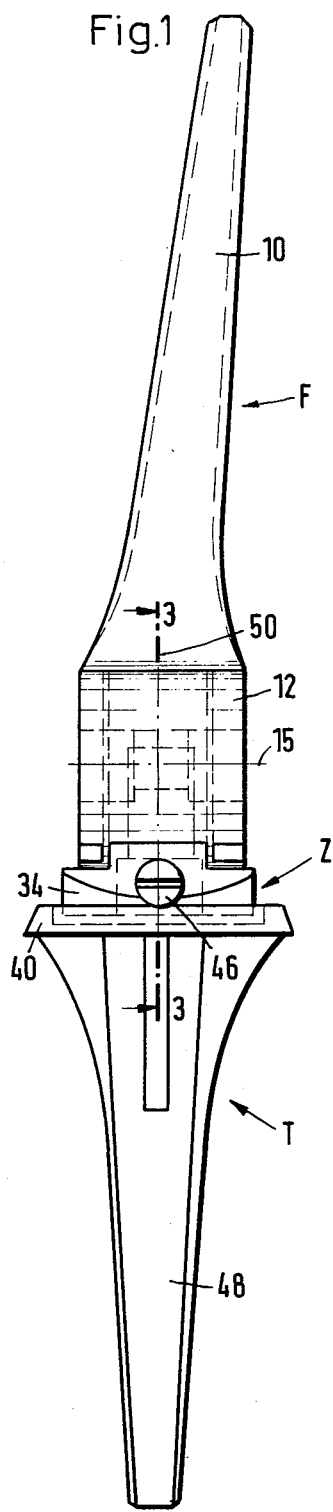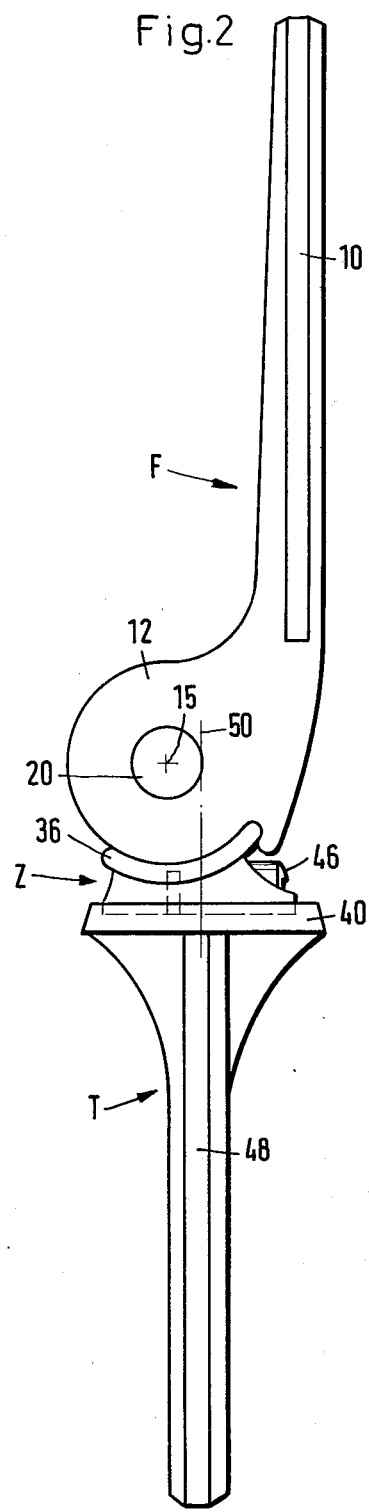

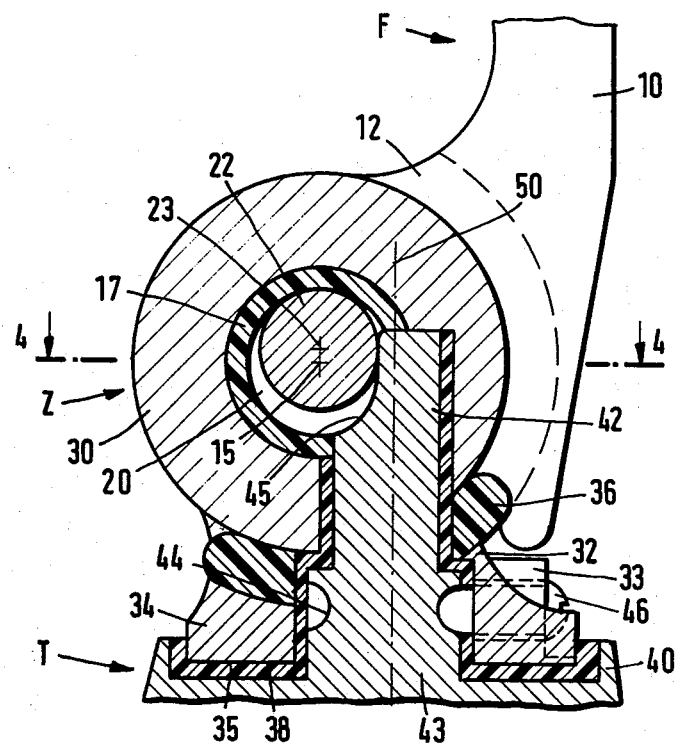
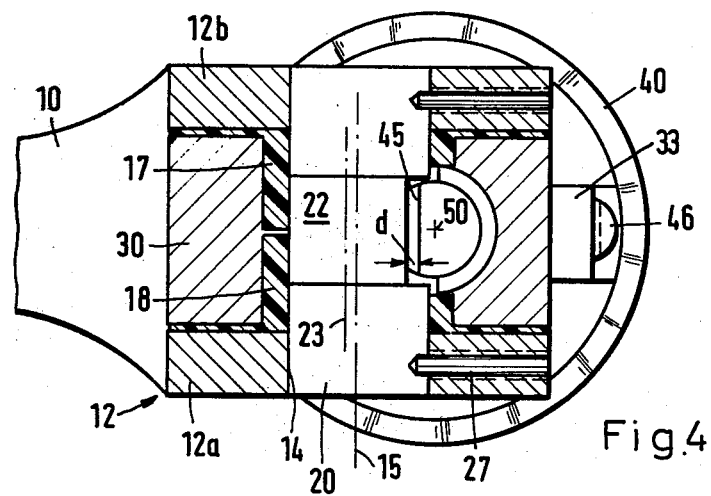

KNEE-JOINT PROSTHESIS

BACKGROUND OF THE INVENTION

The invention relates to an endo knee prosthesis having a femur part and a tibia part which are adapted to be anchored, each by way of an intramedullary stem, in the femur and lower leg bone respectively and which are pivotable relatively to one another around a flexing-axis pin to an extent limited by abutments.

When it becomes necessary to replace a knee joint by a prosthesis as a result of damage due to accident or disease, the operating surgeon will endeavor to resect as little bone as possible and to select a prosthesis which is likely to be highly durable, so that the operation does not have to be repeated and the joint does not stiffen.

In the case of conventional total prostheses, it has been necessary to resect the widened heads from the femur and tibia, whereafter the intramedullary stems on the hinge-like prosthesis are introduced into the medullary cavity of the associated bones and anchored in place by bone cement. Considerable resection is necessary in this procedure and durability is limited since all that secures the prosthesis from turning in the bones is just the bone cement. Consequently, impact torque loadings of the joint occasionally cause the prosthesis to loosen and the loosening is not only painful but makes a further operation necessary.

To obviate these problems, German patent specification No. 2 114 287 proposes that the joint zone of the prosthesis be so narrow that the joint can be implanted inside the femoral head. This step really does obviate the difficulties mentioned by making total resection of the condyle unnecessary. Also, implanting the prosthesis in a recessed part of the condyle provides extra securing against turning. Unfortunately, with the known joint construction two disadvantages arise, for the reason that the prosthesis must be taken apart for implantation and, after the intramedullary stems have been positioned, the prosthesis must be assembled by way of the hinge or pivot pin. Consequently, a bore or recess extending medially through the condyle is necessary for such pin, with a resultant reduction of the unresected part of the condyle. Yet another disadvantage is that for anatomical reasons the bore is required in a part of the condyle where the lateral ligaments are attached, so that such ligaments have to be removed, even though undamaged, and therefore become unavailable to damp forces and to provide additional guiding of the joint.

SUMMARY OF THE INVENTION

It is therefore an object of the invention so to improve the known prostheses that the lateral ligaments do not have to be touched in the implantation operation — i.e., the lateral ligaments can continue to perform their functions after the substitution of the prosthesis for the natural joint.

According to the invention, therefore, in an endo knee prosthesis of the kind described a pivot is fixedly disposed on the tibia or femur part, extends along the longitudinal axis of the tibia part and prolongs whichever part is connected to it towards the other part; and the femur or tibia part is formed with a bore which is adapted to receive the pivot, there being disposed on the last-mentioned part a securing element for securing the pivot in the bore.

As a very advantageous development of such a prosthesis, the femur part is articulated via the flexing-axis pin to an intermediate element which is formed with the pivot-receiving bore and which is so connected via the pivot to the tibia part as to be rotatable, to an extent limited by abutments dependent upon the flexing angle, and releasable. Consequently, and in contrast to the prior art, mobility of the joint is assured not only around the horizontal flexing axis but also around a substantially vertical pivoting axis; there is therefore complete simulation of the natural joint which, when the lower leg bone moves from the extended into the flexed position, permits rotation of the lower leg bone relatively to the femur as well as the bending movement. In both the natural joint and in this further development of the prosthesis according to the invention the amount of pivoting depends upon the angle between the femur and the lower leg bone.

Preferably, the body of rotation is an adjustable eccentric connected to the flexing-axis pin and the flexing-axis pin is mounted relatively to the femur part and intermediate element, and the latter is mounted relatively to the pivot, its bottom part and a bearing surface of the tibia part, in each case by means of at least one plastics bearing element; the plastics bearing elements can be replaceable.

According to another feature of the invention, the eccentric and that part of the pivot which is near the eccentric are enclosed in dust-tight manner, and the securing element is a screw which is preferably self-locking, is screwed into a projection of the intermediate element and engages at its exposed end in an annular groove in the pivot or the bottom part thereof.

BRIEF DESCRIPTION OF THE DRAWINGS

The invention will be described in greater detail hereinafter with reference to the preferred embodiment shown in the drawings wherein:

FIG. 1 is an end view of the endo knee prosthesis in its extended position;

FIG. 2 is a side view of the prosthesis of FIG. 1;

FIG. 3 is a view to an enlarged scale and in section on the line 3—3 of FIG. 1, and FIG. 4 is a section through the prosthesis on the line 4—4 of FIG. 3 but with the joint flexed.

DETAILED DESCRIPTION OF THE INVENTION

An implant endo knee prosthesis to be described hereinafter is subdivided into a femur part F, an intermediate member Z and a tibia part T, and make a hinging movement around a flexing axis 15 between −5° and +145° and also, when flexed, is adapted to make a limited rotation of the order of something like ±20° around the axis of the tibia. The joint embodying the flexing axis is disposed already made up between the femur part F and the intermediate element Z, whereas the rotational bearing is provided between the element Z and the tibia part T and, as will become apparent from the following description, is assembled in the course of the surgical operation.

The femur part F has an intramedullary stem 10 and a fork 12 which, in the view in side elevation in FIG. 2, engages around the flexing axis 15 like a circle segment; the fork 12 is so recessed at its centre and transversely of the axis 15 that two fork arms 12a, 12b arise. The two arms 12a, 12b are formed concentrically of the axis 15 with a bore 14.

The intermediate element Z has a lug 30 which is introducible into the recess of the fork 12 and whose outer periphery is rounded around the axis 15 with the same radius as is the fork 12. A central bore which extends coaxially of the axis 15 and through the lug 30 has a diameter greater than the diameter of the bore 14 by an extent such that the difference between the two diameters allows sufficient space to receive a plastics bearing element subdivided into two bearing parts or shells 17, 18 (see FIG. 4). At assembly the two parts 17, 18 are introduced into the central bore of lug 30. Each part 17, 18 has a side flange. The intermediate element Z then has its lug 30 pushed into the recess of the fork 12 of the femur part F and is secured non-rotatably by the introduction of a flexing-axis pin 20.

The lug 30 is connected via a relatively narrow neck 32 to a circular base 34 whose underside is a base surface 35 adapted to absorb the vertical forces arising in subsequent use.

As can be gathered from FIGS. 3 and 4, the pin 20 is secured against turning and sliding out laterally by means of two screwthreaded pins 27 screwed into corresponding bores in the fork arms 12a, 12b. At its centre the pin 20 takes the form of an eccentric 22 having an eccentric axis 23. As will be described in greater detail hereinafter, the position of eccentric 22 — i.e., the position of its axis 23 — relatively to the flexing axis 15 is a matter of considerable importance in assembly.

A plastics runner 36 pushed over neck 32 of element Z is adapted in its curved outer diameter to the fork 12 and also, as can be gathered from FIGS. 2 and 3, is rounded at both ends. The rounded ends serve as resilient abutments limiting the hinging movement of the prosthesis around the flexing axis 15; as previously stated, in the present embodiment the hinging movement can extend over a region of from $-5°$ to $+145°$. The range of hinging movement can be varied readily by using a differently shaped runner 36.

By way of a plastics bearing element 38 the surface 35 bears rotatably on a correspondingly shaped end plate 40 of the tibia part T. A pivot 42 having a circular base 43 rises from the centre of end plate 40 and serves to centre the intermediate element Z, the same having provision for limited rotation relatively to the tibia part T. The elements 40, 43, 42 are disposed concentrically of a pivot axis 50 which corresponds to the tibia axis and which, as can be seen in FIGS. 3 and 4, is offset from the flexing axis 15; the axis 50 intersects a horizontal (in FIG. 3) axis passing through the flexing axis 15 at right angles.

As can be gathered from FIG. 3, the plastics bearing element 38 separating surface 35 of element Z from the tibia part end plate 40 has a stepped sleeve-like extension which engages intimately around the outer contours of the pivot pin 42 and base 43 and which is preassembled in the combination of the intermediate element Z and the femur part F. The stepped extension is received in a corresponding recess in the element Z and retained by a screw 46 screwed into a tapped bore in a projection 33 of neck 32. The exposed end of screw 46 extends through a lateral bore of bearing element 38, the main function of screw 46 being to serve as a releasable connecting element between the members Z and T. The exposed end of screw 46 engages in an annular groove 44 in base 43. After the femur part F and tibia part T have been introduced into appropriate cavities or recesses or the like in the femur and tibia and embedded with bone cement or the like, all that the operating surgeon has to do is to connect the tibia part T to the intermediate element Z by pushing pivot pin 42 with base 43 into the corresponding recess of the bearing element 38 and tightening the screw 46. The length thereof is such that when its head is in contact with the outside surface of projection 33, the free end of the screw engages in groove 44 but does not contact the base thereof. This ensures that the tibia part T remains rotatable relatively to the intermediate element Z.

As can be seen in FIGS. 3 and 4, the top end of the member 42 is formed on one side with a recess 45 to provide a cooperating surface which, with the device assembled, is near eccentric 22 of flexing-axis pin 20. When the prosthesis is in the extended position shown in FIG. 3, the recess 45 engages with the correspondingly adjusted eccentric 22 without clearance — i.e., when the joint is in the extended position the tibia part T cannot rotate around the axis 50 relatively to the femur part F. However, when the joint is flexed through e.g. 90° in the manner shown in FIG. 4, there is a gap $d$ between the eccentric 22 and the recess 45, the gap enabling the whole tibia part T to turn to either hand until the outside edges of recess 45 abut the eccentric 22. Thus, the eccentric 22 and cooperating surface provided by recess 45 form an abduction and rotation abutment in which both permissable abduction and rotation of the joint are controlled by the abutment of the pin and pivot. The angle of rotation can be adapted to the rotatability when flexed of a natural knee joint by appropriate adjustment of the eccentric 22 and is somewhere around $\pm 20°$.

All bearing areas of the endo knee prosthesis hereinbefore described are lined with an appropriate plastics ensuring freedom from wear and a long working life. The risk of metal abrasion is therefore completely obviated, and so there is no risk of metallosis. The only metal parts which engage directly with one another are the eccentric 22 and the surfaces of the recess 45. However, these metal parts are completely enclosed, and so any metal abrasion occurring cannot be washed out into the organism.

The subassembly comprising the femur part F and intermediate element Z with the flexing joint, such unit being adapted to be implanted in the completely prefabricated state, is relatively narrow near the fork 12 and can be completely received in a prepared condylar cavity.

We claim:

1. A joint prosthesis having a flexing-axis pin having a flexing axis, first and second parts which are adapted to be anchored in first and second bones, respectively, on opposite sides of said joint and which are pivotable through a range of flexing angle relative to one another about said flexing-axis pin, said joint prosthesis further comprising:

a pivot disposed on one of said first and second parts and extending along the longitudinal axis of that part on which it is disposed; and an intermediate element having a pin receiving bore for receiving said flexing-axis pin, a pivot-receiving bore for receiving said pivot and a securing element for securing said pivot in said pivot-receiving bore, the central portion of said flexing-axis pin together with said pivot forming an abduction and rotation abutment in which the amount of permissible of rotation is dependent on the flexing angle.

2. A prosthesis according to claim 1, characterised in that the abduction and rotation abutment is formed by a body of rotation having an axis parallel to but offset from the flexing axis and by a cooperating surface on said pivot, the spacing between said body of rotation and said cooperating surface being determined by the flexing angle of said joint such that the body of rotation makes complete contact with the cooperating surface in the extended position of the prosthesis but only partial contact in the flexed position of the prosthesis.

3. A prosthesis according to claim 2, characterized in that the body of rotation is an adjustable eccentric connected to the flexing-axis pin.

4. A prosthesis according to claim 2, characterised in that said first part further comprises fork arms for receiving said flexing-axis pin, said pin being secured to said fork arms by screwthreaded pins in order to prevent relative displacement and rotation between said body of rotation and said first part.

5. A prosthesis according to claim 1, characterised in that the flexing-axis pin is mounted relatively to the first part and intermediate element, and the latter is mounted relatively to the pivot and said second part, in each case by means of at least one plastics bearing element.

6. A prosthesis according to claim 5, characterised in that the plastics bearing elements are replaceable.

7. A prothesis according to claim 5, characterised in that the bearing elements for the flexing-axis pin is a flanged sleeve combined from two parts.

8. A prosthesis according to claim 1, characterised in that a plastics runner is disposed on said intermediate element and the range of said flexing angle is determined in one direction by the abutment of said first part against said intermediate element and in the other direction by the abutment of said first part with said plastics runner.

9. A prosthesis according to claim 3, characterised in that the eccentric and that part of the pivot which is near the eccentric are enclosed in dust-tight manner.

10. A prosthesis according to claim 1, characterised in that the securing element is a screw which is preferably self-locking, is screwed into a projection of the intermediate element and engages at its exposed inner end in an annular groove in the pivot.

* * * * *